United States Patent [19]

Giacalone et al.

[11] Patent Number: 4,615,692
[45] Date of Patent: Oct. 7, 1986

[54] PORTABLE FEMALE CATHETER

[76] Inventors: Joseph J. Giacalone; Joseph S. Giacalone, both of 2547 La Serena, Escondido, Calif. 92025

[21] Appl. No.: 784,953

[22] Filed: Oct. 7, 1985

[51] Int. Cl.$^4$ ........................ A61M 11/00; A61M 5/32
[52] U.S. Cl. ...................... 604/94; 604/329; 604/330; 604/179; 604/174; 128/761
[58] Field of Search ................ 604/94, 327, 328, 329, 604/330, 331, 174, 179; 128/761

[56] References Cited

U.S. PATENT DOCUMENTS

| 3,722,503 | 3/1973 | Hovick | 128/761 |
| 3,895,629 | 7/1975 | Snyder | 604/179 |
| 3,938,521 | 2/1976 | Ritota et al. | 604/329 |
| 4,563,183 | 1/1986 | Barrodale | 604/329 |

Primary Examiner—C. Fred Rosenbaum
Assistant Examiner—Gene B. Kartchner
Attorney, Agent, or Firm—Frank D. Gilliam

[57] ABSTRACT

A portable catheter for use by females suffering from urinary incontinency. A short catheter is held in place extending a short distance into the urethra by means which permits the wearer substantially full freedom of movement. A relatively stiff shield is fastened to an undergarment in a manner holding the shield in position adjacent to the wearer's urethral and vaginal openings. A plug means is fastened to the shield in a manner permitting it to be inserted into the vagina to help hold the shield in position. The generally tubular catheter includes locking washer means riding in a slot in said shield allowing the spacing between the catheter and vaginal plug to be varied to accommodate varying physical dimensions. A drain plug extends from the external end of the catheter to drain urine to a conventional collection bag which may, for example, be secured to the user's leg. In use, the user slips the garment over her legs, bringing the vaginal plug and catheter end into proximity to the vagina and urethra, respectively. The catheter and vaginal plug are then inserted into the respective openings, the garment is pulled into comfortable engagement with the body, and the catheter is connected to the urine collecting bag. The user can then be confident that the catheter will remain in place despite body movements.

11 Claims, 3 Drawing Figures

PORTABLE FEMALE CATHETER

BACKGROUND OF THE INVENTION

This invention relates in general to medical devices for use in cases of urinary incontinence and, more specifically, to a portable catheter adapted for use by females.

Urinary incontinency due to medical or physiological reasons is a problem for a significant number of women. The problem may range from an occasional release of a small amount of urine when the women sneezes, coughs or laughs to total loss of control of the urethral sphincter, as in the case of a paraplegic who has lost all feeling and muscle control below the waist.

In the past, an absorbent pad, such as a sanitary napkin worn against the urethral opening was sufficient for the person suffering only occasional urine release, but not for those who had total loss of sphincter control. For those women, a catheter of the Foley or balloon type had to be nearly continuously worn, extending entirely through the urethra into the bladder. Such a catheter consists basically of a hollow tube having parallel thereto a thin air tube with an expansible, ring-like balloon at the distal end. The catheter would be inserted into the bladder through the urethra, then the balloon would be expanded sufficiently to prevent withdrawal without first deflating the balloon. With this catheter, urine could continuously drain from the bladder, through openings in the distal end of the catheter, then through a drain tube connected to the proximal end of the catheter into a collection bag typically strapped to the user's leg.

While such catheters are successful in draining urine, they present a number of problems. Great care must be used when moving the person using the catheter to prevent accidentally pulling and partially withdrawing the catheter or over-inserting it, which severly limits the mobility of the user. Care and skill must be used in inserting and removing the catheter to assure the proper length is inserted, the balloon is expanded to the proper extent and the balloon is fully deflated prior to removal.

Generally the portion of the catheter extending out of the body must be taped to the skin to keep the catheter in place. This often results in sores or infections at the tape site. Also, urine may leak out along the outside of the catheter resulting in embarrassing odors and stains as the user moves and jostles the catheter since the outside diameter of the catheter must be somewhat smaller than the inside diameter of the urethra to permit the catheter to be pushed entirely through the urethra.

The greatest problem with long-term use of such catheters extending all the way into the bladder is the very serious risk of infection in the bladder and/or urethra. Treatment of such infections is difficult and slow, with many chronic infections. Such infections can be very serious and can lead to death, especially with partially paralyzed women.

Thus, there is a continuing need for improved devices and methods for draining urine from the urethra of women having little or no control of urine release, which can more easily be emplaced and replaced, which permit free movement of ambulatory women and which both reduce the chance of infection and improve the chances of successfully treating any infection that does occur.

SUMMARY OF THE INVENTION

The above-noted problems, and others, are overcome in accordance with our invention by a portable catheter assembly for use by women which basically comprises a contoured, somewhat stiff, shield fastened to an undergarment in a manner positioning the shield over the urethral and vaginal openings when the garment is worn by a female, a plug means fastened to the shield adapted to be inserted in the vagina to help hold the shield in position, and a short catheter tube mounted on said shield in a manner allowing limited movement toward and away from said vaginal plug to accommodate anatomical variations in users, the catheter adapted to being inserted a short distance into the urethra as the vaginal plug is inserted into the vagina when the shield is moved into position. The catheter has a diameter resulting in a snug fit of the catheter in the urethra and the distal end thereof preferrably includes both an end hole and side holes near the distal end to receive urine from the urethra. The proximal end of the catheter is adapted to having a drain tube attached thereto to allow urine to drain into any suitable collecting device, such as a plastic bag secured to the user's leg.

This system permits the user to move about (or be moved in the case of a paralyzed women) with little risk of disloding the catheter. Even if the catheter is dislodged, since it is very short none of the injury which would occur if a conventional balloon catheter was dislodged is likely. Further, the risk of infection is greatly reduced since the catheter does not extend into the bladder and does not contact the entire urethra. Any infection which might occur is more easily treated, since the irritant of the long catheter extending into the bladder is eliminated.

BRIEF DESCRIPTION OF THE DRAWING

Details of the invention, and of preferred embodiments thereof will be further understood upon reference to the drawing, wherein.

DETAILED DESCRIPTION OF THE INVENTION

Figure 1:
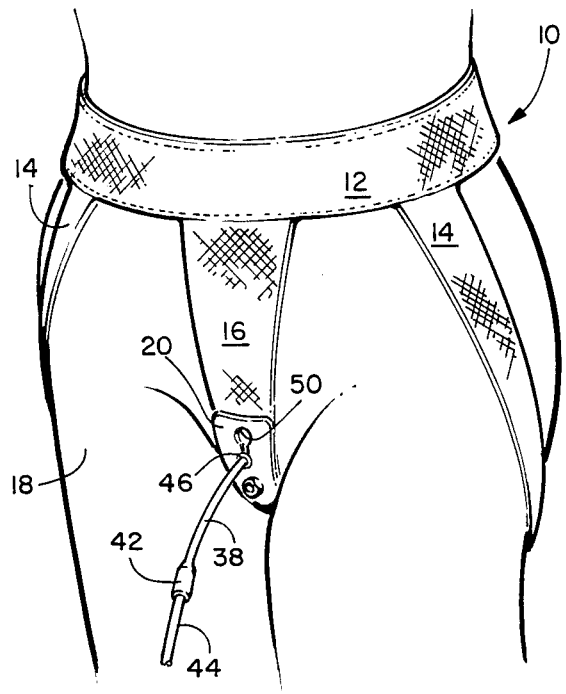
FIG. 1 is a perspective view of the portable catheter as worn by a female.

Referring now to FIG. 1, there is seen an undergarment 10 made up of a waist-encircling strap 12, two side straps 14 and a front strap 16, all in place on a lower female torso 18. Each of these straps may be made from any suitable material, such as the elasticized cotton material used in men's athletic supporters. This preferred undergarment is in general similar to a men's athletic supporter without the cup. The upper ends of straps 14 and 16 are fastened to waist strap 12 in any conventional manner, such as sewing. The lower ends of the two straps 14 and strap 16 are fastened together, such as by sewing, towards the back of the crotch. Garment 10 is put on in the usual manner, by slipping it on over the feet and pulling it up over the legs and into place. While this strap-type garment is preferred for ease of use and accuracy of placement of the shield, as detailed below, a panty-type garment could be used if desired.

Figure 2:
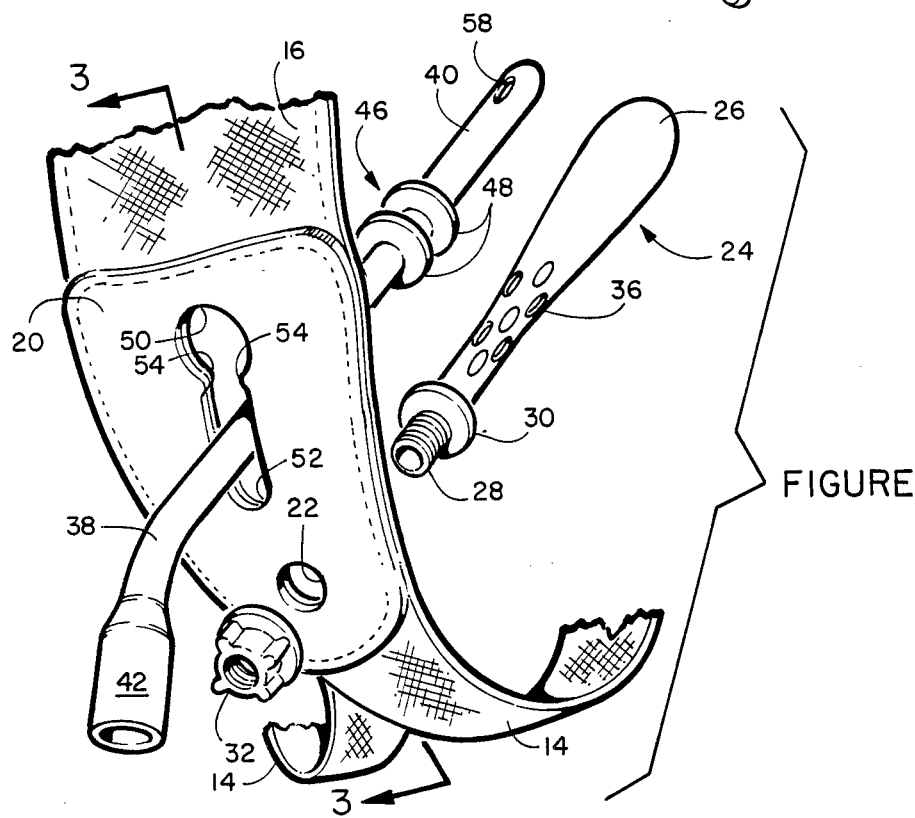
FIG. 2 is a partially exploded perspective view of the primary components of the portable catheter system.

As best seen in FIGS. 1 and 2, a shield means 20 is fastened, such as by sewing or adhesive means, to the lower front portion of front strap 16, in a position to cover the urethra and vagina of the lower torso 18 when the garment 10 is properly fitted in place. Shield 20 may be made from any suitable material. The material should be soft for comfort but fairly stiff to retain its shape and should have a smooth, impervious surface to prevent absorption of urine or other liquids and to permit easy cleaning. Plastic materials such as polypropylene, polyethylene, acrylics, styrenes or the like are preferred. Best results have been obtained with polypropylene, which has the optimum combination of flexibility and stiffness is easily cleaned and resists cracking despite continuous flexing. While the ideal thickness for shield 20 depends upon the material, in general thicknesses in the 0.025 to 0.100 inch are effective. With polypropylene, a thickness of about 0.050 inch provides the optimum combination of flexibility, stiffness and light weight.

Figure 3:
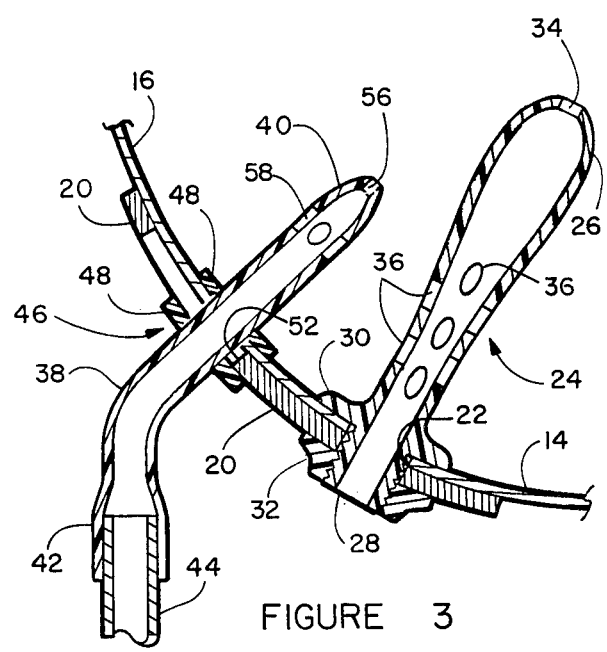
FIG. 3 is a section view taken on line 3—3 in FIG. 2 of the primary components of the portable catheter system.

Shield 20 has a hole 22 (as seen in FIGS. 2 and 3) positioned adjacent to the user's vagina. A vaginal plug 24 having an elongated vagina penetrating first end 26 and a threaded second end 28 adjacent a flange 30 has the threaded end inserted in hole 22. Flange 30 engages the inner surface of strap 16 adjacent to hole 22 and nut 32 is threaded finger-tight onto threaded end 28 to engage the outer surface of shield 20 adjacent to hole 22. As is further detailed below, first end 26 is positioned in the user's vagina to resist movement of shield 20 in the approximate plane of the user's skin in the crotch area. First end 26 of vaginal plus 24 has an opening 34 in the distal end and a plurality of holes 36 in the sides for maximum sanitary conditions. Plug 24 may be fabricated from any suitable material which is fluid impervious, easily cleaned and has the desired combination of flexibility and stiffness. Many plastics are suitable, but we have found that polyproplyene provides the optimum combination of characteristics. While the plug 24 may have any suitable dimensions, we have found that a length of about 3.5 inches from the second end to flange 30 and a diameter of about 0.5 inch produce optimum results. The threads between end 28 and nut 32 may, for example be standard ¼-20 threads.

A catheter tube 38 is provided having a perforated distal end 40 and an enlarged proximal end 42 adapted to connection to a drain tube 44 for draining urine into a conventional receptacle (not shown). A locking washer means 46 is provided to maintain catheter tube in the desired position substantially perpendicular to shield 20, and permit limited movement along a line toward and away from vaginal plug 24 while substantially preventing movement transverse to that line. Locking washer means 46 typically includes two spaced washers 48. Washers 48 may be heat welded or adhesively bonded to catheter tube 38 after proper adjustment to fit a specific person, or may simply be a very tight friction fit thereover. If desired, washers 48 could be flanges on a very short tube sized to slip over catheter tube 38 and be secured thereto.

Shield 20 has a hole 50 spaced from hole 22 and having a diameter just sufficient to allow catheter end 40 and locking washers 48 to be inserted therethrough. A slot 52 in shield 20 along a line between urethral and vaginal openings communicates with hole 50. The width of slot 52 corresponds to the diameter of catheter 38. A pair of inwardly-extending projections 54 along slot adjacent to hole 50 are sized to allow catheter tube 38 to "snap" (with slight compression) between hole 50 and slot 52. Catheter tube 38 is assembled to shield 20 by inserting the end 40 into hole 50 until washers 48 are aligned with the outside surfaces of shield 20 and strap 16 in the region of hole 50. Washers 48 are spaced apart a distance equal to the combined thickness of shield 20 and front strap 16, as seen in FIG. 3. Catheter 38 is then pressed towards slot 52 until the tube snaps past projections 54 and enters slot 52. The center point of slot 52 is spaced from the center of vaginal plug 24 a distance corresponding to the average distance between vaginal and urethral openings in women. Catheter 38 can be easily moved back and forth in slot 52 to accommodate an individual's anatomical differences in this distance. While it is preferred that hole 50 be located at the end of slot 52 opposite hole 22 to avoid weakening shield 20 between those holes, the hole 50 could be at either end of slot 50, if desired.

The distal end 40 of catheter tube 38 has an end hole 56 and a plurality holes 58 (preferably two) near the end. Catheter tube typically has an outside diameter of about ¼ inch. Our catheter tube can be somewhat wider, and fit considerably more snugly in the urethra, than can a conventional bladder catheter, since it need only be pushed a short distance into the urethra, while a conventional Foley catheter must slip through the entire length of the urethra to the bladder. Therefore, the snug fit combined with the ring of holes 58 substantially prevents leakage of urine down the outside of the catheter which often occurs with Foley catheters, causing odor, stains and embarrassment.

In use either a new, sterile, assembly is used or a previously used assembly is disassembled by removing nut 32 and plug 24 and removing catheter tube 38 through hole 50. Each component may be easily cleaned, sterilized or replaced, as desired. The system is then assembled by inserting plug 24 in hole 22 and tightening nut 32 finger tight, then inserting catheter tube 38 into hole 50 and snapping the tube past projections 54 into slot 52. Proximal end 42 is secured to a conventional drain tube 44 to drain urine to a conventional receiving bag (not shown) which may be secured to the leg of an ambulatory person, to a hospital bed, or the like. The woman then slips garment 10 over the feet and legs, with one leg between each side strap 14 and front strap 16. When the garment is nearly in place, she adjusts the position of catheter tube 38 along slot 52 so that vaginal plug 24 and catheter tube 40 can be substantially simultaneously inserted as the garment is drawn into wearing position. The woman may then dress in normal garments, such as slacks or dresses and perform most normal activities without fear of dislodging or damaging the catheter or fear of urine leakage. From time to time the assembly may be removed for cleaning or replacement.

Other applications, variations and ramifications of this invention will occur to those skilled in the art upon reference to the present disclosure. Those are intended to be included within this invention, as defined in the appended claims.

We claim:
1. A portable catheter for females which comprises:
   a shield means secured to an undergarment in a manner positioning said shield over the urethral and vaginal openings when said garment is worn;

a plug means fastened to said shield and adapted to being inserted in the vagina to help hold said shield means in position; and catheter means including a catheter tube supported by mounting means on said shield so that said catheter tube extends a short distance substantially perpendicularly from said shield and is adapted to being inserted in the urethra when said plug is inserted into the vagina;

said mounting means including slot means in said shield extending along the line extending from vagina to urethra and beyond and locking means permitting movement of said catheter tube along said slot but substantially in no other direction.

2. The portable catheter for females according to claim 1 wherein said undergarment comprises:

a first elastic strap adapted to encircle the waist of a user;

two elastic side straps fastened to said waist strap and each adapted to partially encircle the lower edge of one of the users buttocks; and an elastic front strap fastened to the front of said first strap between said side straps and adapted to extend downwardly and fasten to the lower ends of said side straps in the rearward crotch area of a user;

said shield fastened to said first strap in a position covering the vaginal and urethral openings when said garment is in place on a user's body.

3. The portable catheter for females according to claim 1 wherein said shield is formed from polypropylene and has a thickness of about 0.05 inch.

4. The portable catheter for females according to claim 1 wherein:

said shield has a first hole located over the vaginal opening of a user when said garment is in place on a user's body;

said plug means includes an elongated distal end portion adapted to be inserted into a user's vagina;

the proximal end of said plug having a threaded end portion having a diameter suitable for insertion through said first hole;

a flange on said plug adjacent to said threaded portion; and a nut means adapted to thread onto said threaded portion and clamp said shield and front strap material around said first hole between said flange and said nut.

5. The portable catheter for females according to claim 4 wherein said elongated distal end has a length of from about 3 to 4 inches.

6. The portable catheter for females according to claim 5 wherein said elongated distal end is formed from polypropylene, has an opening at the distal end and has a plurality of openings along the sides thereof.

7. The portable catheter for females according to claim 1 wherein said catheter means includes:

said short catheter tube at one end having a diameter sufficient to fit snugly in an urethra and having at least one urine-admitting opening; and connection means at the other end of said catheter tube adapted to operatively connect to a urine drain tube.

8. The portable catheter for females according to claim 7 wherein:

The center of said slot lies at a distance from said first hole approximately equal to the average distance between vaginal and urethral openings, the length of said slot being approximately equal to the normal variations in that distance, the width of said slot being substantially equal to the outside diameter of said catheter tube;

a second hole in said shield in communication with one end of said slot;

said locking means on said catheter tube comprising a pair of spaced washers fastened to said catheter tube, said washers having a diameter such as to permit the catheter and locking means to be inserted in said second hole, then moved toward said slot with washers on opposite sides of said shield; and inwardly extending projections at the interface between said second hole and said slot so that said catheter tube can be snapped past said projections into said slot and retained therein;

whereby said catheter tube is held in a position substantially perpendicular to said shield and prevented from significant movement in any direction except toward and away from said vaginal plug, so that anatomical differences in distances between urethral and vaginal openings may be accommodated.

9. The portable catheter for females according to claim 8 wherein said distal end of said catheter tube has an opening in the end and openings in the catheter wall adjacent to said end.

10. The portable catheter for females according to claim 9 wherein the openings in the catheter wall number two.

11. The portable catheter for females according to claim 8 wherein the length of said catheter from said locking means to the distal end is about 1 inch and said catheter tube is formed from polypropylene.

* * * * *